(12) United States Patent
Limousin

(10) Patent No.: US 8,391,976 B2
(45) Date of Patent: Mar. 5, 2013

(54) SYSTEM AND METHOD FOR CARDIAC RESYNCHRONIZATION THERAPY WITH OPTIMIZATION OF EFFORT-BASED RATE-RESPONSIVE PACING

(75) Inventor: Marcel Limousin, Paris (FR)

(73) Assignee: Sorin CRM S.A.S., Clamart (FR)

( * ) Notice: Subject to any disclaimer, the term of this patent is extended or adjusted under 35 U.S.C. 154(b) by 151 days.

(21) Appl. No.: 12/953,090

(22) Filed: Nov. 23, 2010

(65) Prior Publication Data
US 2011/0125209 A1     May 26, 2011

(30) Foreign Application Priority Data
Nov. 23, 2009   (FR) ..................... 09 58279

(51) Int. Cl.
*A61N 1/00* (2006.01)
*A61B 5/02* (2006.01)
*A61B 5/04* (2006.01)

(52) U.S. Cl. .............. 607/17; 607/5; 607/6; 607/18; 607/19; 600/481; 600/483; 600/519

(58) Field of Classification Search ......... 607/4–38, 607/119–132; 600/373–375, 449–450, 481–503, 600/508–528
See application file for complete search history.

(56) References Cited

U.S. PATENT DOCUMENTS

| | | | |
|---|---|---|---|
| 5,134,997 A | | 8/1992 | Bennett et al. |
| 5,158,078 A | * | 10/1992 | Bennett et al. .............. 607/27 |
| 5,609,613 A | | 3/1997 | Woodson et al. |
| 5,722,996 A | | 3/1998 | Bonnet et al. |
| 6,556,866 B2 | | 4/2003 | Dal Molin et al. |
| 6,622,039 B1 | | 9/2003 | Ripart et al. |
| 2005/0137635 A1 | | 6/2005 | Molin |

FOREIGN PATENT DOCUMENTS

| | | |
|---|---|---|
| EP | 0750920 | 1/1997 |
| EP | 1059099 | 12/2000 |
| EP | 1108446 | 6/2001 |
| EP | 1524009 | 4/2005 |
| WO | WO 9203182 | 3/1992 |

OTHER PUBLICATIONS

Foreign Search Report (Annexe Au Rapport De Recherche Preliminaire Relatif A La Demand De Brevet Francais No. FR0958279 FA729740), Jul. 28, 2010.

* cited by examiner

*Primary Examiner* — Niketa Patel
*Assistant Examiner* — Lindsey G Hankins
(74) *Attorney, Agent, or Firm* — Orrick Herrington & Sutcliffe, LLP

(57) ABSTRACT

An active implantable medical device for cardiac resynchronization therapy with effort based rate-responsive pacing is described. The device calculates a rate-responsive stimulation frequency based on output signal of an effort sensor between a base frequency ($f_{base}$) and a maximum frequency ($f_{max}$). The device determines a target stimulation frequency based on the difference between a first frequency and the maximum frequency ($f_{max}$). The first frequency is the higher frequency of the base frequency ($f_{base}$) and the spontaneous frequency of the patient. The device calculates a stimulation frequency that has an immediate increase in the pacing rate from the higher of the initial value of the current stimulation frequency, or the spontaneous frequency to the target stimulation frequency, within a predetermined time, or a predetermined number of cardiac cycles. A plurality of consecutive effort zones (Z1-Z4) is defined over the extent of the dynamic range of the output signal of the effort sensor.

6 Claims, 1 Drawing Sheet

SYSTEM AND METHOD FOR CARDIAC RESYNCHRONIZATION THERAPY WITH OPTIMIZATION OF EFFORT-BASED RATE-RESPONSIVE PACING

The present application claims the benefit of French Application No. 09-58137 entitled "Active Implantable Medical Device For Cardiac Resynchronization With Optimization of Effort Rate Responsive Pacing" and filed Nov. 23, 2009, which is hereby incorporated by reference in its entirety.

FIELD

The present invention relates to "active implantable medical devices" as defined by the 20 Jun. 1990 Directive 90/385/EEC of the Council of the European Communities, and more particularly to devices that continuously monitor a patient's cardiac rhythm and deliver to the patient's heart, if necessary, electrical pulses for stimulating left and the right ventricles and resynchronizing them using a technique known as Cardiac Resynchronization Therapy ("CRT") or Biventricular Pacing ("BVP").

BACKGROUND

It is known to implant into a patient a CRT pacemaker with electrodes to stimulate both left and right ventricles of the patient. Such devices typically continuously monitor the patient's heart rhythm and deliver, if necessary, electrical pulses to concurrently stimulate the left and right ventricles to resynchronize them. An interventricular delay ("DVV" or "VVD") can be applied between the respective moments of stimulation in the two ventricles and adjusted to resynchronize the contraction of both ventricles to optimize the patient's hemodynamic status. One such CRT pacemaker is disclosed, for example, in EP 1108446 A1 and its counterpart U.S. Pat. No. 6,556,866 (assigned to Sorin CRM, previously known as ELA Medical).

Similar to conventional pacemakers, a CRT pacemaker can be rate-responsive including means for controlling the rate of the pacing pulses according to the level of a patient effort. A lower pacing rate is delivered when the patient is at rest, and a gradually increasing pacing rate is delivered as the patient's effort increases. The parameter for determining a patient's effort is measured by an appropriate sensor or combination of sensors, such as a physiological sensor (e.g., a minute ventilation sensor or "MV sensor") and/or a physical activity sensor (e.g., an accelerometer or "G Sensor").

The rate-responsive pacing rate can vary between a minimum frequency referred to as a "base frequency" ($f_{base}$) and a maximum frequency ($f_{max}$) that defines a maximum value for the pacing rate calculated by a rate-responsive algorithm. It should be understood, however, that the instantaneous frequency of a patient's heart rate may be either a spontaneous frequency (e.g., a sinus rhythm) or a stimulated pulse frequency, and that in the latter case, the stimulation pulse frequency is managed by the pacemaker according to the level of patient effort.

EP1059099A1 and its counterpart U.S. Pat. No. 6,622,039 (assigned to Sorin CRM, previously known as ELA Medical) describe a CRT pacemaker providing with a long-term adjustment of the $f_{max}$ parameter according to the changes in the patient's general condition.

A typical indication for use of a CRT pacemaker is a heart failure condition arising from dilated cardiac cavities together with a significantly reduced ejection fraction and a rapid exhaustion of the patient even in the case of a slight effort being exerted by the patient. For healthy people, during an effort, the heart puts into action two mechanisms to meet increasing hemodynamic needs. First, there is an increase in a heart rate (i.e., spontaneous frequency or sinus rhythm). Second, there is an adaptation of contractility (which affects the ejected volumes). However, in the presence of a heart failure condition, the patient has little adaptability with respect to the contractility of heart muscle.

In addition, patients suffering from heart failure are generally under intensive medical treatment, including administration of a beta-blocker medication to slow their heart rate, and their average spontaneous frequency at rest is generally higher than that of healthy patients. However, these beta-blockers and other drug treatments have an effect of reducing the capacity of the heart rate acceleration. This results in a lower reactivity during an effort.

As a consequence, for patients with class II heart failure as classified by the New York Heart Association ("NYHA") standards, a rapid exhaustion follows in a moderate patient effort. For patients classified in NYHA classes III and IV, a rapid exhaustion occurs irrespective of the level of patient effort or exercise even for simple activities of everyday life.

It is known that using multisite stimulation for CRT can alleviate some of the consequences of heart failure through better synchronization between the two ventricles. The alleviation is achieved by increasing contractility and increasing the filling phase of the cardiac chambers. However, due to the use of beta-blockers, even in the case of a little patient effort, the responsiveness of a heart rate increase is limited by the negative chronotropic effect of these drug treatments.

Known multisite CRT pacemaker devices may include algorithms to control the rate-responsive pacing. WO 92/03182 A1 describes a conventional single chamber, rate-responsive pacemaker but it does not have CRT functionality. The rate-response in such a device is designed to be as physiological as possible, therefore it provides a slow and progressive variation in the order of several tens of seconds. In one example, such a device provides a transition from the base frequency to the maximum frequency over about sixty seconds.

Such a prior art rate-responsive algorithm, originally intended for a patient suffering from bradycardia, does not produce a desired result for a patient suffering from a cardiac heart failure. Indeed, it may produce an adverse effect. For example, if at the beginning of the patient's effort the patient is in spontaneous rhythm with a frequency greater than the pacing rate calculated by the rate-responsive pacing algorithm, the patient is not stimulated. This induces an additional delay until the algorithm adapts the rate-responsive rate corresponding to the patient's effort level, because the patient only benefits from the rate-responsive feature when a stimulation frequency calculated by the algorithm is higher than the current spontaneous frequency of the patient.

On the other hand, the profile for increasing the pacing rate in the rate-response algorithm is intended to apply a slow and gradual increase in frequency, especially at the beginning of the patient effort. In this case, when the patient begins to be stimulated, the frequency increases slowly for a moderate effort, with a greater acceleration slope only for sustained efforts. Such a frequency rate response profile is, therefore, poorly suited to patients suffering from a heart failure condition because such patients in general rarely perform sustained efforts. As a result, they do not have a significant and rapid increase in their heart rate, and the dynamics of the heart rate increase is limited by the negative chronotropic effect of drug treatments administered to them.

SUMMARY AND OBJECTS

It is therefore an object of the present invention to provide an implantable CRT device that has a rate-responsive pacing algorithm with a profile suitable for patients classified with a heart failure indication. Those patients are suited for this type of device overcoming various drawbacks of the prior art devices as described above.

According to one embodiment, the present invention is directed to a CRT pacemaker, for example, of a type disclosed in EP 1108446 A1 and its counterpart U.S. Pat. No. 6,556,866, or EP 1059099 A1 and its counterpart U.S. Pat. No. 6,622,039. The CRT pacemaker includes a circuit and/or a control logic for determining a current value of a spontaneous frequency of the patient in the presence of a sinus rhythm, an effort sensor that delivers an output signal representative of the current level of a patient effort. The CRT pacemaker detects the beginning of an effort from the output signal delivered by the effort sensor, calculates a stimulation frequency that varies between a base frequency and a maximum frequency according to the output signal delivered by the effort sensor, and selectively delivers stimulation pulses at the calculated stimulation frequency.

According to an embodiment of the present invention, the CRT device provides an accelerated increase of the stimulation frequency by: (i) determining a target frequency based on the difference between a first frequency and the maximum frequency, wherein the first frequency is the higher frequency of the base frequency and the spontaneous frequency, and (ii) directly increasing, on an early detection of an effort, the stimulation frequency from the initial value of the current pacing rate, or, where appropriate, the spontaneous frequency, to the target frequency. The increase is performed either in a predetermined time or in a predetermined number of cardiac cycles. More preferably, the accelerated increase is achieved in no more than four cardiac cycles.

In one embodiment of the present invention, the CRT device defines and responds to a plurality of consecutive areas of effort spanning the dynamic range of the output signal delivered by the effort sensor. This allows for accelerating the increment of the stimulation frequency separately for each consecutive area of effort. For each area of effort defined by a sub-range of the effort sensor output signal, a target frequency is determined when the output signal delivered by the effort sensor reaches the sub-range, and the stimulation frequency directly increases to the target frequency. In this embodiment, the target frequency of a given area is based on the difference between the target frequency of the area immediately below the area corresponding to the current information of the effort sensor and the maximum frequency.

In a preferred embodiment, the consecutive areas of effort are defined by an equal division of the dynamic range of the output signal delivered by the effort sensor. The dynamic range of the output signal delivered by the effort sensor may be monitored, and the device updates the dynamic range and redefines the size and/or the number of the plurality of consecutive areas of effort.

In one embodiment, the target frequency is determined by a percentage, for example, 50% of the difference between a first frequency and the maximum frequency. The first frequency as noted is determined as the higher frequency of the base frequency and the spontaneous frequency, where applicable. The predetermined number of cardiac cycles to reach the target frequency is preferably no more than four cycles.

BRIEF DESCRIPTION OF THE DRAWINGS

Further features, characteristics and advantages of the present invention will become apparent to a person of ordinary skill in the art from the following detailed description of embodiments of the present invention, made with reference to the drawings annexed, in which like reference characters refer to like elements and in which.

DETAILED DESCRIPTION

Figure 1:
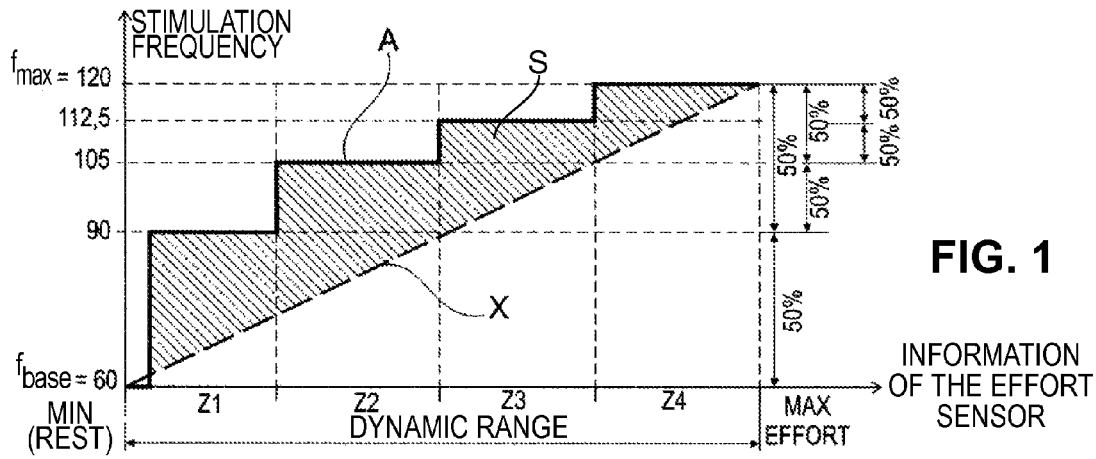
FIG. 1 schematically shows a characteristic of an exemplary stimulation frequency according to output signals generated by an effort sensor of a CRT pacemaker, according to the prior art and the present invention.
Figure 2:
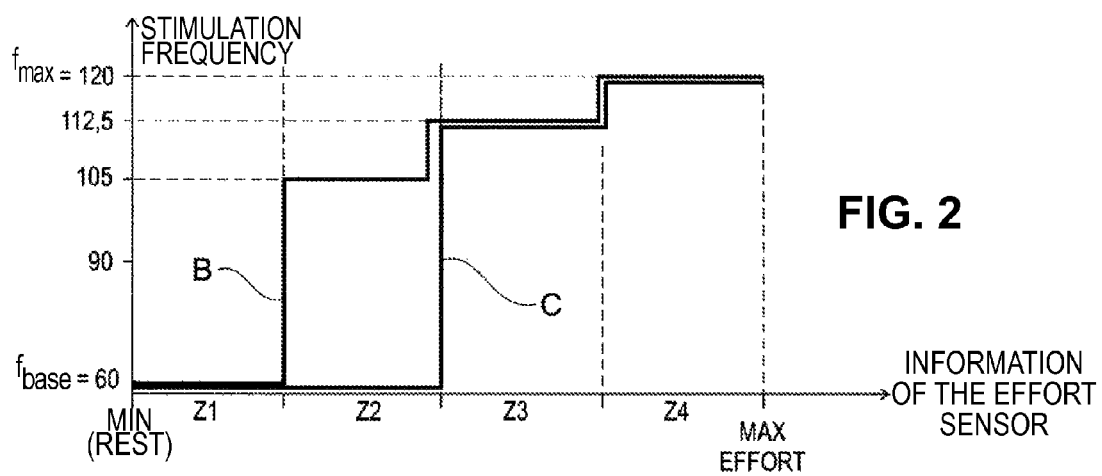
FIG. 2 illustrates a faster rate-responsive feature of the present invention in the case of an exemplary situation of stimulated rhythm, according to one embodiment.
Figure 3:
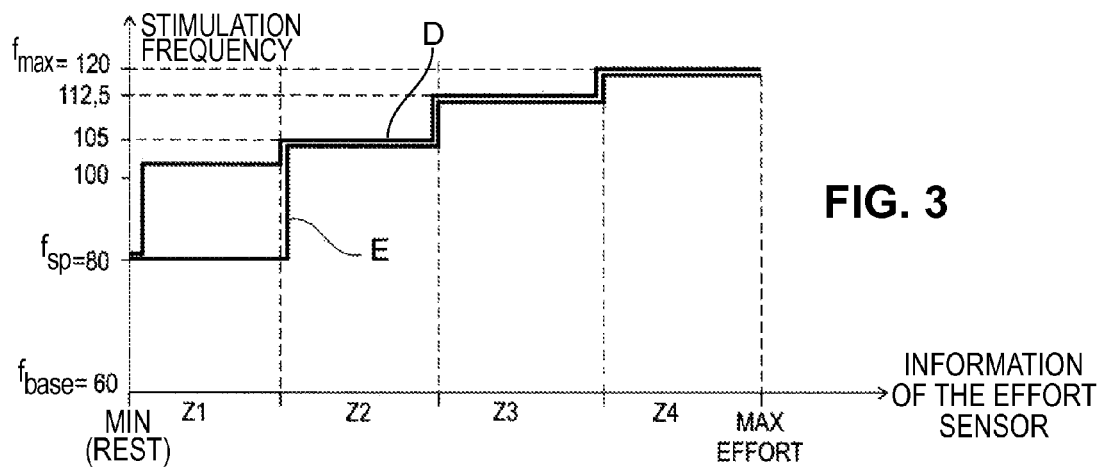
FIG. 3 is illustrates a faster rate-responsive feature of the present invention in an exemplary situation of spontaneous rhythm, according to one embodiment.

With reference to FIGS. 1-3, detailed description of various embodiments according to the present invention are described below.

In a preferred embodiment, the present invention and its functionality are implemented by an appropriate programming of the control software of a known device, for example, a cardiac pacemaker or a defibrillator/cardioverter, including circuits, hardware and/or control logic for collecting a signal from endocardial leads and/or one or more sensors.

The present invention may particularly be applied to implantable devices such as those of the Ovatio CRT or Paradym CRT device families produced and marketed by Sorin CRM, Clamart France, formerly known as ELA Medical, Montrouge, France. These devices include programmable microprocessor and memory devices to receive, format, and process electrical signals collected (detected) by implanted electrodes and deliver stimulation pulses to the implanted electrodes. It is possible to transmit by telemetry software to the implantable devices. The transmitted software is stored in a memory of the implantable devices and is executed to implement various functions of the present invention as described herein. The adaptation of these devices to implement the functions and features of the present invention is believed to be within the abilities of a person of ordinary skill in the art, and therefore will not be described in detail.

According to one embodiment, the device includes various means for providing resynchronized ventricular pacing, with control over the frequency of stimulation according to the patient's level of effort when the patient is not experiencing spontaneous rhythm. The device may include one or more effort sensors including a physiological sensor and/or an activity sensor. A physiological sensor is intended to provide an adequate representation of the instantaneous metabolic needs of the patient at a given time. One suitable physiological sensor is a minute ventilation sensor ("sensor MV"). An activity sensor detects a rapid change in the activity of the patient, and typically is an accelerometer sensor ("sensor G") although other types of activity sensors may be used. More preferably, the device is equipped with both types of sensors to operate in a "cross watch" mode for their respective indications by combining their indications to provide information representative of the level of a patient effort, (hereinafter designated "Information of the effort sensor") to appropriately control the heart rate of the patient. The sensor, or combination of sensors, delivering a sensor signal is generally referred to as "effort sensor", although the term is not restricted to any particular type of sensor.

In general, the patient's heart rate is either a spontaneous frequency (also referred to as a "sinus rhythm") or a stimulated frequency (also known as the "pacing rate"). The stimulated frequency occurs in the absence of a spontaneous frequency or when the control algorithm estimates that the spontaneous rhythm is incompatible with the level of a patient effort.

According to one embodiment, the stimulation frequency is managed by a servo device that manages the frequency of stimulation. The stimulation frequency varies the pacing rate between a minimum value referred to as a "base frequency" ($f_{base}$), for example, 60 bpm, and a maximum frequency ($f_{max}$), for example, 120 bpm. The initial values of these two extreme frequencies are typically parameterized and programmed into the implantable driver by a physician, and are regularly updated by the device during manual or auto-calibration phases carried out, according to techniques of the prior art which will not be described herein with details. A stimulation frequency at $f_{base}$ corresponds to the minimum value of information of the effort sensor (e.g., a null value in the case of an effort sensor being an accelerometer). A stimulation frequency at $f_{max}$ corresponds to the maximum output signal of the effort sensor or of the cross watch of multiple effort sensors when multiple effort sensors are employed. The difference between these two extreme information of the effort sensor defines the dynamic range of the effort sensor.

FIG. 1 illustrates a control characteristic of the stimulation frequency versus the information of the effort sensor. In a conventional device, the control characteristic corresponds to the characteristic X that shows a substantially linear characteristic of the stimulation frequency increasing with the level of effort indicated by the effort sensor, from the base frequency $f_{base}$ to the maximum frequency $f_{max}$. In accordance with the present invention, however, while maintaining the same extreme frequencies (base frequency $f_{base}$ for the minimum effort and maximum frequency $f_{max}$ for maximum effort), the control characteristic follows a different pattern of the stimulation frequency, with a more rapid acceleration for moderate patient efforts. Significantly, for patients with a heart failure, such moderate efforts are (i) the most commonly occurring activity because such patients rarely perform sustained efforts, and (ii) the most poorly compensated by prior known techniques, for the reasons explained above including the dual consequence of the chronotropic effect of beta-blockers and of the inadequacy of current rate-responsive device algorithms.

Further in accordance with the present invention, upon detection of an early effort, the device calculates a target frequency based on the difference between the base frequency $f_{base}$ (or the current spontaneous or stimulated frequency) and the maximum frequency $f_{max}$, and controls the device to reach the target frequency in a low number of cardiac cycles, for example, 3 to 4 cardiac cycles. The target frequency may in particular be a percentage, for example, 30 or 50% of the difference between the base frequency (or the current frequency) and the maximum frequency.

According to one embodiment, the present technique for determining stimulation frequency is selectively applied on several distinct areas or zones of the dynamic range of the effort sensor. For each given area, the difference between the target frequency of the area immediately below (instead of using the base frequency) and the maximum frequency $f_{max}$, is calculated. More specifically, as shown in FIG. 1, the dynamic range of the effort sensor is, for example, divided into four zones, namely Z1 to Z4. These areas are consecutive over the extent of the dynamic range of the information of the effort sensor. In the illustrated example, the four zones Z1 to Z4 are of equal extent, each covering 25% of the dynamic range of the effort sensor output signal, but this characteristic is not limiting, and may alternatively consist of a different division of the successive zones, with narrower zones for the smallest levels of effort (e.g., Z1, or Z1 and Z2) in order to provide greater acceleration in these areas corresponding to moderate potential efforts when a greater reactivity is desirable and beneficial.

With reference to FIG. 1, a control characteristic A, according to the invention, illustrates the stimulation frequency versus the information of the effort sensor, is determined as follows.

For a patient in a stimulated state, the stimulation frequency is initially (at rest) the base frequency $f_{base}$, for example, 60 bpm. With a moderate effort, the effort sensor output signal provides information corresponding to zone Z1. The device calculates a target frequency, for example, corresponding to half the interval between the base frequency $f_{base}$ (e.g., 60 bpm) and the programmed maximum frequency $f_{max}$ (e.g., 120 bpm), namely a target frequency equal to: 60+50% (120−60)=90 bpm.

If the effort continues to increase, the information of the effort sensor increases and reach zone Z2. The next target frequency calculation is similarly performed, but instead of using the base frequency $f_{base}$, the target frequency of zone Z1 (90 bpm) is used. This provides for zone Z2 a new target frequency equal to: 90+50% (120−90)=105 bpm.

The same process is applied for calculating target frequency of Z3 zone, which yields: 105+50% (120−105)=112.5 bpm.

As to the target frequency of Z4 zone of the most intense patient effort, it is automatically set to the maximum frequency, which is 120 bpm in this example.

In a progressive effort where the information of the effort sensor passes successively through the entire dynamic zones from Z1 to Z4, the characteristic A referenced in FIG. 1 is obtained.

It is observed that for a moderate effort, the acceleration of the heart rate according to the control characteristic A of the present invention is above the control characteristic X that is provided by a conventional rate-response control algorithm. The shaded area S between the characteristics A and X is referred to as a "cardiac reserve" that allows increasing the patient's cardiac output, because the increased heart rate leads to an increase in cardiac output.

FIG. 2 illustrates an exemplary case where a patient makes an increased effort, with information of the effort sensor being located immediately in zone Z2, without passing through zone Z1. For such an increased effort, without crossing zone Z1, the target frequency is calculated according to the technique described above, but is increased with a higher percentage from 25% to 50% to ensure a higher stimulation frequency. This corresponds to the characteristic B.

The same adjustment technique may be applied in case of an even more increased effort, with information of the effort sensor being located immediately in zone Z3, without passing through zones Z1 and Z2. This corresponds to the characteristic C in FIG. 2. To achieve this faster adaptation, the algorithm examines in a given zone (Z2 or Z3) whether or not the characteristic has already gone through the preceding zones (Z1 or Z2).

FIG. 3 illustrates an exemplary characteristic of stimulation frequency versus information of the effort sensor as shown in FIG. 1, but in the example, the patient has a spontaneous frequency at rest. The spontaneous frequency $f_{sp}$ is generally higher than the base frequency $f_{base}$, in this example $f_{sp}$ is 80 bpm. The calculation of the target frequency is carried out as described above for the example of FIG. 1 for a stimulated frequency, but the spontaneous frequency $f_{sp}$ is substituted with the base frequency $f_{base}$ in the calculation. With the maximum frequency $f_{max}$ of 120 bpm, the target frequency of zone Z1 is calculated to be: 80+50% (120−80)=100 bpm.

The present invention, in calculating the target frequency, considers the fastest route from the base frequency $f_{base}$ (or the spontaneous current frequency $f_{sp}$ when appropriate) for the patient's condition. This ensures that the frequency increment calculated by the algorithm and applied by the device is significant enough to support the patient's effort. In one example, a target frequency in the presence of a spontaneous rhythm is calculated to be 100 bpm (i.e., an additional frequency increase of 20 bpm) instead of 90 bpm in the case of a stimulated rhythm as shown in FIG. 1. The characteristic corresponding to this spontaneous rhythm situation is illustrated as the control characteristic D in FIG. 3. In the case of an increased effort placing information of the effort sensor directly in zone Z2 without going through zone Z1, the resulting control characteristic is illustrated as the control characteristic E in FIG. 3.

One skilled in the art will appreciate that the present invention may be practiced by other than the embodiments described above, which are provided for purposes of illustration, and not of limitation.

The invention claimed is:

1. An active implantable medical device for treating a heart failure condition with cardiac resynchronization therapy (CRT) and/or with synchronized stimulation, comprising:
   an effort sensor providing an output signal representative of a current level of a patient's effort; and
   a CRT pacemaker having electrodes configured to determine a spontaneous frequency ($f_{sp}$) of a patient in the presence of a sinus rhythm and control logic configured to detect a beginning of the patient's effort from the output signal, stimulation frequency varying between a base frequency ($f_{base}$) and a maximum frequency ($f_{max}$) according to the output signal, and selectively delivering stimulation pulses according to said effort stimulation frequency, said control logic selectively delivering stimulation pulses for CRT via incrementing said delivered pulse stimulation frequency by:
   determining a target frequency based on a difference between a first frequency and the maximum frequency ($f_{max}$), wherein the first frequency is the higher frequency of the base frequency ($f_{base}$) and the spontaneous frequency ($f_{sp}$); and
   increasing, in response to a detection of the beginning of the patient's effort, the stimulation frequency from an initial value or the spontaneous frequency to said target frequency in a predetermined time period corresponding to the time period of no more than four cardiac cycles.

2. The device of claim 1, wherein the output signal of the effort sensor has a dynamic range, the control logic being provided and configured to define a plurality of consecutive effort zones corresponding to the dynamic range of the output signal of the effort sensor, determining when the output signal of the effort sensor increases from a preceding effort zone to a consecutive effort zone, and wherein incrementing said delivered pulse stimulation frequency determines, separately for each consecutive effort zone, said target frequency and an increase of the delivered stimulation frequency to said determined target frequency, the determined target frequency of each consecutive effort zone being based on the difference between the target frequency of the preceding effort zone and the maximum frequency ($f_{max}$).

3. The device of claim 2, wherein said plurality of consecutive effort zones are defined by an equal division of the dynamic range of the output signal of the effort sensor.

4. The device of claim 2, further comprising means for updating the dynamic range of the output signal of the effort sensor, and redefining the corresponding plurality of consecutive effort zones to the updated dynamic range.

5. The device of claim 1, wherein said control logic is configured to determine the target frequency determines a percentage of the difference between the first frequency and the maximum frequency ($f_{max}$).

6. The device of claim 5, wherein said percentage is 50%.

* * * * *